(12) United States Patent
Migneco et al.

(10) Patent No.: US 11,135,950 B2
(45) Date of Patent: Oct. 5, 2021

(54) THERAPEUTIC TECHNOLOGY FUSION

(71) Applicant: Lear Corporation, Southfield, MI (US)

(72) Inventors: Francesco Migneco, Saline, MI (US); David Gallagher, Sterling Heights, MI (US)

(73) Assignee: Lear Corporation, Southfield, MI (US)

( * ) Notice: Subject to any disclaimer, the term of this patent is extended or adjusted under 35 U.S.C. 154(b) by 59 days.

(21) Appl. No.: 16/704,593

(22) Filed: Dec. 5, 2019

(65) Prior Publication Data
US 2021/0170926 A1   Jun. 10, 2021

(51) Int. Cl.
| | |
|---|---|
| *B60N 2/56* | (2006.01) |
| *B60N 2/90* | (2018.01) |
| *B60N 2/00* | (2006.01) |
| *B60N 2/66* | (2006.01) |
| *A61N 2/02* | (2006.01) |
| *A61N 1/40* | (2006.01) |
| *A61H 9/00* | (2006.01) |
| *A61F 7/00* | (2006.01) |

(52) U.S. Cl.
CPC .............. *B60N 2/5678* (2013.01); *A61F 7/00* (2013.01); *A61H 9/0078* (2013.01); *A61N 1/40* (2013.01); *A61N 2/02* (2013.01); *B60N 2/002* (2013.01); *B60N 2/5692* (2013.01); *B60N 2/665* (2015.04); *B60N 2/914* (2018.02); *B60N 2/99* (2018.02); *A61H 2201/0149* (2013.01); *A61H 2201/10* (2013.01)

(58) Field of Classification Search
CPC ........ B60N 2/5678; B60N 2/665; B60N 2/99; B60N 2/914; B60N 2/002; B60N 2/5692
USPC .......................................... 297/180.1–180.16
See application file for complete search history.

(56) References Cited

U.S. PATENT DOCUMENTS

| | | | | |
|---|---|---|---|---|
| 7,511,833 | B2 * | 3/2009 | Breed ................ | G01F 23/0076 180/272 |
| 7,866,017 | B2 * | 1/2011 | Knoll ................... | B60N 2/5685 29/91.1 |
| 10,034,631 | B1 | 7/2018 | Gallagher et al. | |
| 10,210,409 | B1 | 2/2019 | Migneco et al. | |
| 10,213,147 | B2 | 2/2019 | Gallagher et al. | |
| 2003/0209893 | A1 * | 11/2003 | Breed .................. | B60N 2/0248 280/735 |
| 2004/0129478 | A1 * | 7/2004 | Breed .................. | B60N 2/0276 180/273 |
| 2005/0131607 | A1 * | 6/2005 | Breed ................ | B60R 21/0152 701/45 |
| 2005/0192727 | A1 * | 9/2005 | Shostak .............. | B60C 23/041 701/37 |
| 2006/0217864 | A1 * | 9/2006 | Johnson ............... | B60N 2/067 701/45 |

(Continued)

*Primary Examiner* — Rodney B White
(74) *Attorney, Agent, or Firm* — MacMillan, Sobanski & Todd, LLC (57) ABSTRACT

A system having a controller includes one or more thermal generation element assemblies, or a plurality of air bladder assemblies, or a plurality of electromagnetic coil assemblies, or a combination thereof, that are in communication with the controller and are configured for activation by the controller. The one or more thermal generation element assemblies, or the plurality of air bladder assemblies, or the plurality of electromagnetic coil assemblies, or a combination thereof are configured to provide a holistic mitigating effect on a vehicle occupant confined within the interior space of a vehicle for long periods of time.

20 Claims, 5 Drawing Sheets

(56) References Cited

U.S. PATENT DOCUMENTS

| | | | | |
|---|---|---|---|---|
| 2006/0251293 A1* | 11/2006 | Piirainen | | B60R 21/01516 382/104 |
| 2007/0085697 A1* | 4/2007 | Breed | | B60N 2/002 340/4.62 |
| 2007/0156317 A1* | 7/2007 | Breed | | B60R 21/01516 701/45 |
| 2007/0271014 A1* | 11/2007 | Breed | | B60R 19/483 701/31.9 |
| 2008/0036580 A1* | 2/2008 | Breed | | G01S 15/04 340/438 |
| 2008/0065291 A1* | 3/2008 | Breed | | G06K 9/00355 701/36 |
| 2008/0100706 A1* | 5/2008 | Breed | | B60R 21/01526 348/143 |
| 2008/0142713 A1* | 6/2008 | Breed | | B60R 21/01516 250/330 |
| 2008/0157940 A1* | 7/2008 | Breed | | B60N 2/853 340/425.5 |
| 2008/0161989 A1* | 7/2008 | Breed | | B60R 21/01532 701/31.4 |
| 2008/0174423 A1* | 7/2008 | Breed | | B60R 21/01542 340/539.22 |
| 2008/0216567 A1* | 9/2008 | Breed | | B60N 2/888 73/146.5 |
| 2008/0234899 A1* | 9/2008 | Breed | | B60N 2/0232 701/47 |
| 2008/0284575 A1* | 11/2008 | Breed | | H01H 35/146 340/438 |
| 2009/0046538 A1* | 2/2009 | Breed | | B60R 25/102 367/93 |
| 2009/0058593 A1* | 3/2009 | Breed | | G01S 15/88 340/5.2 |
| 2009/0066065 A1* | 3/2009 | Breed | | B60R 25/257 280/735 |
| 2009/0092284 A1* | 4/2009 | Breed | | B60N 2/002 382/103 |
| 2010/0207431 A1* | 8/2010 | Petzel | | B60N 2/643 297/180.16 |
| 2011/0095940 A1* | 4/2011 | Breed | | B60C 11/24 342/146 |
| 2012/0089299 A1* | 4/2012 | Breed | | B60N 2/888 701/36 |
| 2018/0178694 A1* | 6/2018 | McMillen | | B60N 2/666 |
| 2018/0345833 A1 | 12/2018 | Gallagher et al. | | |
| 2019/0193591 A1 | 6/2019 | Migneco et al. | | |

* cited by examiner

THERAPEUTIC TECHNOLOGY FUSION

BACKGROUND OF THE INVENTION

Vehicles, such as the non-limiting examples of automobiles, trucks, buses, and the like, can include one or more seats for supporting occupants during use. A typical vehicle seat can include a seat cushion portion and a back portion, each of which can include a structural frame having occupant supporting and cushioning features.

The seat cushion portion and the back portion can be pivotally attached to one another, enabling the seat cushion portion and the back portion to assume differing positions relative to each other.

In the event an occupant is supported by the seat and confined within the vehicle for a lengthy period of time, the occupant can experience physiological discomfort. It would be desirable to provide a vehicle seat that provides effective relief of physiological discomfort experienced by an occupant confined within the vehicle for a lengthy period of time.

SUMMARY OF THE INVENTION

It should be appreciated that this Summary is provided to introduce a selection of concepts in a simplified form, the concepts being further described below in the Detailed Description. This Summary is not intended to identify key features or essential features of this disclosure, nor is it intended to limit the scope of the therapeutic technology fusion.

The above objects as well as other objects not specifically enumerated are achieved by a system having a controller. One or more thermal generation element assemblies, or a plurality of air bladder assemblies, or a plurality of electromagnetic coil assemblies, or a combination thereof are in communication with the controller and are configured for activation by the controller. The one or more thermal generation element assemblies, or the plurality of air bladder assemblies, or the plurality of electromagnetic coil assemblies, or a combination thereof, are configured to provide a holistic mitigating effect on a vehicle occupant confined within the interior space of a vehicle for a long period of time.

The above objects as well as other objects not specifically enumerated are also achieved by a vehicle system including a controller positioned within a vehicle. One or more thermal generation element assemblies, or a plurality of air bladder assemblies, or a plurality of electromagnetic coil assemblies, or a combination thereof, are positioned in the vehicle and are in communication with the controller. The one or more thermal generation element assemblies, or the plurality of air bladder assemblies, or the plurality of electromagnetic coil assemblies, or a combination thereof, are configured to provide a holistic mitigating effect on a vehicle occupant confined within the interior space of a vehicle for a long period of time.

The above objects, as well as other objects not specifically enumerated, are also achieved by a method that includes the steps of positioning one or more thermal generation element assemblies, or a plurality of air bladder assemblies, or a plurality of electromagnetic coil assemblies within a vehicle seat assembly and activating the one or more thermal generation element assemblies, or the plurality of air bladder assemblies, or the plurality of electromagnetic coil assemblies to provide a holistic mitigating effect on a vehicle occupant confined within the interior space of a vehicle for a long period of time.

Various aspects of the therapeutic technology fusion will become apparent to those skilled in the art from the following detailed description of the illustrated embodiments, when read in light of the accompanying drawings.

DETAILED DESCRIPTION OF THE PREFERRED EMBODIMENTS

The therapeutic technology fusion of this invention will now be described with occasional reference to specific embodiments. The therapeutic technology fusion may, however, be embodied in different forms and should not be construed as limited to the embodiments set forth herein. Rather, these embodiments are provided so that this disclosure will be thorough and complete, and will fully convey the scope of the therapeutic technology fusion to those skilled in the art.

Unless otherwise defined, all technical and scientific terms used herein have the same meaning as commonly understood by one of ordinary skill in the art to which the therapeutic technology fusion belongs. The terminology used in the description of the therapeutic technology fusion is for describing particular embodiments only and is not intended to be limiting of the therapeutic technology fusion. As used in the description of the therapeutic technology fusion and the appended claims, the singular forms "a," "an," and "the" are intended to include the plural forms as well, unless the context clearly indicates otherwise.

Unless otherwise indicated, all numbers expressing quantities of dimensions such as length, width, height, and so forth as used in the specification and claims are to be understood as being modified in all instances by the term "about." Accordingly, unless otherwise indicated, the numerical properties set forth in the specification and claims are approximations that may vary depending on the desired properties sought to be obtained in the embodiments of the therapeutic technology fusion. Notwithstanding that the numerical ranges and parameters setting forth the broad scope of the therapeutic technology fusion are approximations, the numerical values set forth in the specific examples are reported as precisely as possible. Any numerical values, however, inherently contain certain errors necessarily resulting from error found in their respective measurements.

The description and figures disclose a holistic seating system that combines a plurality of individual therapeutic technologies into a single system that is configured to provide a plurality of responses when activated. As used herein, the term "holistic" is defined to mean addressing the well-being of the whole person. The therapeutic technologies are configured to mitigate the effects on the whole person of being confined within the interior space of a vehicle for a long period of time. Once activated, the plurality of individual therapeutic technologies is configured to provide comfort to the occupant.

Figure 1:
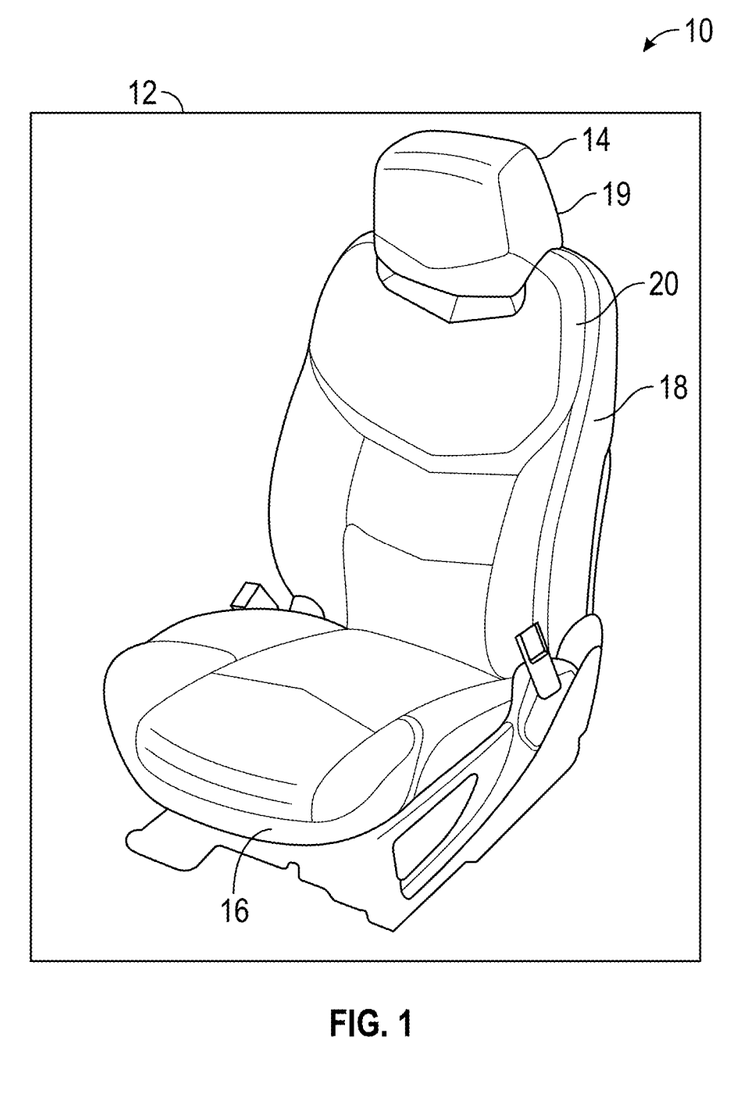
FIG. 1 is a perspective side view of a seat assembly in accordance with this invention.

Referring now to the drawings, there is illustrated in FIG. 1 a vehicle seating system 10 in accordance with the invention. The vehicle seating system 10 is implemented within the interior of a vehicle 12. The vehicle 12 may be a car, truck, or the like. The vehicle seating system 10 includes one or more seat assemblies 14.

The seat assembly 14 includes a seat bottom (i.e., a seat cushion) 16 and a seat back 18. The seat bottom 16 is configured to support the sitting region of a person sitting in the seat assembly 14. The seat bottom 16 can be fixed to a floor of the vehicle on slidable rails (not shown for purposes of clarity). The seat back 18 is configured to support the back of the person sitting in the seat assembly 14. A head restraint 19 may be positioned at the top of the seat back 18.

The seat back 18 is pivotably connected to the seat bottom 16 and is configured to extend upright relative to the seat bottom 16. The seat assembly 14 further includes a cover 20, which covers or upholsters the seat bottom 16 and the seat back 18.

Referring again to FIG. 1, the seat assembly 14 includes a holistic seating system having a plurality of therapeutic technologies configured to provide comfort to an occupant. In the illustrated embodiment, the therapeutic technologies include massage therapy, localized heating or cooling therapy, pulsed electromagnetic field therapy (PEMF), and transcutaneous electrical nerve stimulation therapy (TENS). However, it should be appreciated that in other embodiments, the plurality of therapeutic technologies can include other therapeutic technologies configured to provide comfort to an occupant.

Figure 2:
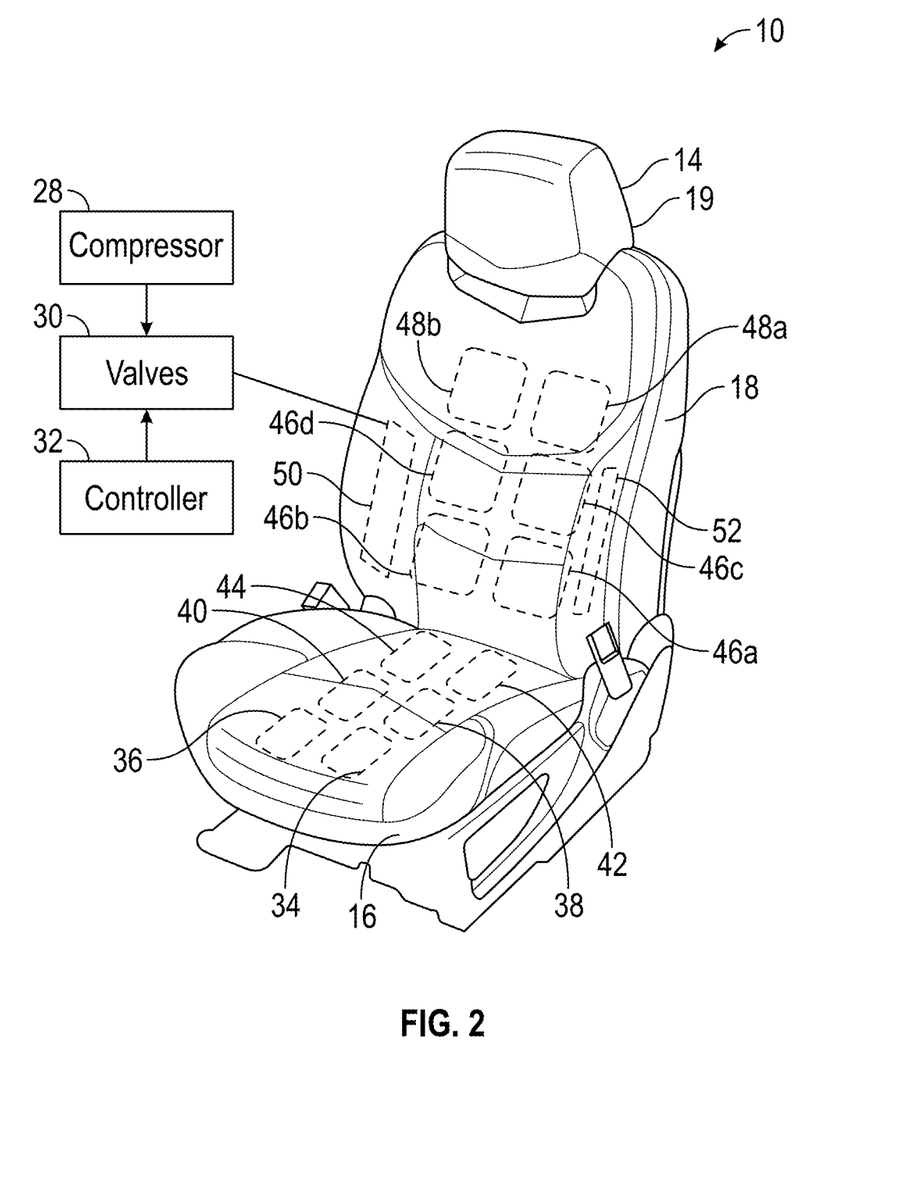
FIG. 2 is a perspective view of the seat assembly of FIG. 1 equipped with a massage therapy therapeutic technology.

Referring now to FIG. 2 and as described above, the seat assembly 14 includes a massage therapeutic technology. One non-limiting example of a massage therapeutic technology is that described in U.S. Patent Application Publication No. 2019/0193591A1, which is incorporated in its entirety herein by reference and, for that reason, is only briefly described.

Referring again to FIG. 2, the seat assembly 14 has at least one compressor and/or pump 28 that is configured to provide a source of compressed air to the seat assembly 14. A plurality of valves 30 are configured to receive the compressed air and are controlled by a controller 32 for regulating compressed air into and out of the seat assembly 14. The seat bottom 16 includes a plurality of pneumatic elements, such as air bladder assemblies 34, 36, 38, 40, 42, and 44. The seat back 18 includes a plurality of lumbar air bladder assemblies 46a-46d, a plurality of upper, mid, and lower thoracic air bladder assemblies 48a and 48b, an upper and lower left side bolster air bladder assembly 50, and an upper and lower right-side bolster air bladder assembly 52. Although one arrangement of air bladder assemblies 34, 36, 38, 40, 42, 44, 46a-46d, 48a, 48b, 50, and 52 is illustrated, any quantity and arrangement of air bladder assemblies may be employed.

Referring again to FIG. 2, the valves 30 may be provided as a common valve bank that is housed in the seat back 26 or under the seat cushion 22. Alternatively, the valves 30 may each be provided on each of the air bladder assemblies 34, 36, 38, 40, 42, 44, 46, 48, 50, and 52. The compressor 28 may be provided in the seat back 26, the seat cushion 22, or concealed elsewhere within the vehicle body 24. The controller 32 may be provided in a module under the seat cushion 22 and may be a multifunction controller that also controls other functions in the vehicle.

Referring again to FIG. 2, the controller 32 is configured to balance the air pressure in opposing air bladders to balance the occupant seating position. It should also be appreciated that in other embodiments, the air bladder assemblies 34, 36, 38, 40, 42, 44, 46a-46d, 48a, 48b, 50, and 52 may be manually activated.

Referring again to FIG. 2, the seating system 10 can be manually or automatically activated in response to repetitive-pattern motions (known as "fidgets") that are characteristic of an occupant that is in pain, distress, or otherwise in physical discomfort. In the event a seated occupant is experiencing pain or discomfort, an instinctive reaction is to fidget or move away from the discomfort. The discomfort may also be caused from fatigue, such as when the occupant sits for too long and blood is not sufficiently circulating. The fidget is an instinctive attempt by the occupant to remove pressure from the area of pain or discomfort. It should also be appreciated that the seating system 10 can be manually or automatically activated by other occupant-related conditions. Non-limiting examples of other occupant-related conditions include drowsiness, stress, fatigue, and the like. In certain instances, the occupant-related conditions can be detected by structures configured to monitor the occupant's heart rate, breathing rate, respiration rate, and the like.

Referring again to FIG. 2, in certain embodiments, the controller 32 can be configured to sense the repetitive pattern and/or other occupant-related condition and offer countermeasures to eliminate the source of pain or discomfort, such as active repositioning, rhythmic inflation-deflation of the bladders to mimic massage, low frequency repositioning inflation, and/or deflation of the air bladder assemblies 34, 36, 38, 40, 42, 44, 46a-46d, 48a, 48b, 50, and 52 situated in the seat bottom 16 and back 18 to generate massage, repositioning, and a side-to-side and fore-aft shifting of the body weight to reduce pressure, pain, and discomfort generated by a stationary position. According to one example, the air bladder assemblies 34, 36, 38, 40, 42, 44, 46a-46d, 48a, 48b, 50, and 52 inflate and deflate for each direction of shifting within a period of thirty seconds or more to reduce occupant perception and to maintain a constant movement, such as a counter fidget. However, it is contemplated that the time period may be occupant specific and may, for example, be up to fifteen minutes. In still other embodiments, the time period may be dictated by manual activation. In still other embodiments, it is contemplated that the massage created by the rhythmic inflation-deflation of the air bladder assemblies 34, 36, 38, 40, 42, 44, 46a-46d, 48a, 48b, 50, and 52 can be used for various occupant-related pain syndromes. In one non-limiting example, the massage is applied to the muscles of the occupant from which the pain originates. In another embodiment, the massage can be used in an acupressure-type system to massage so-called external trigger points of the occupant's body reflecting a referred pain from an originating internal organ.

Figure 3:
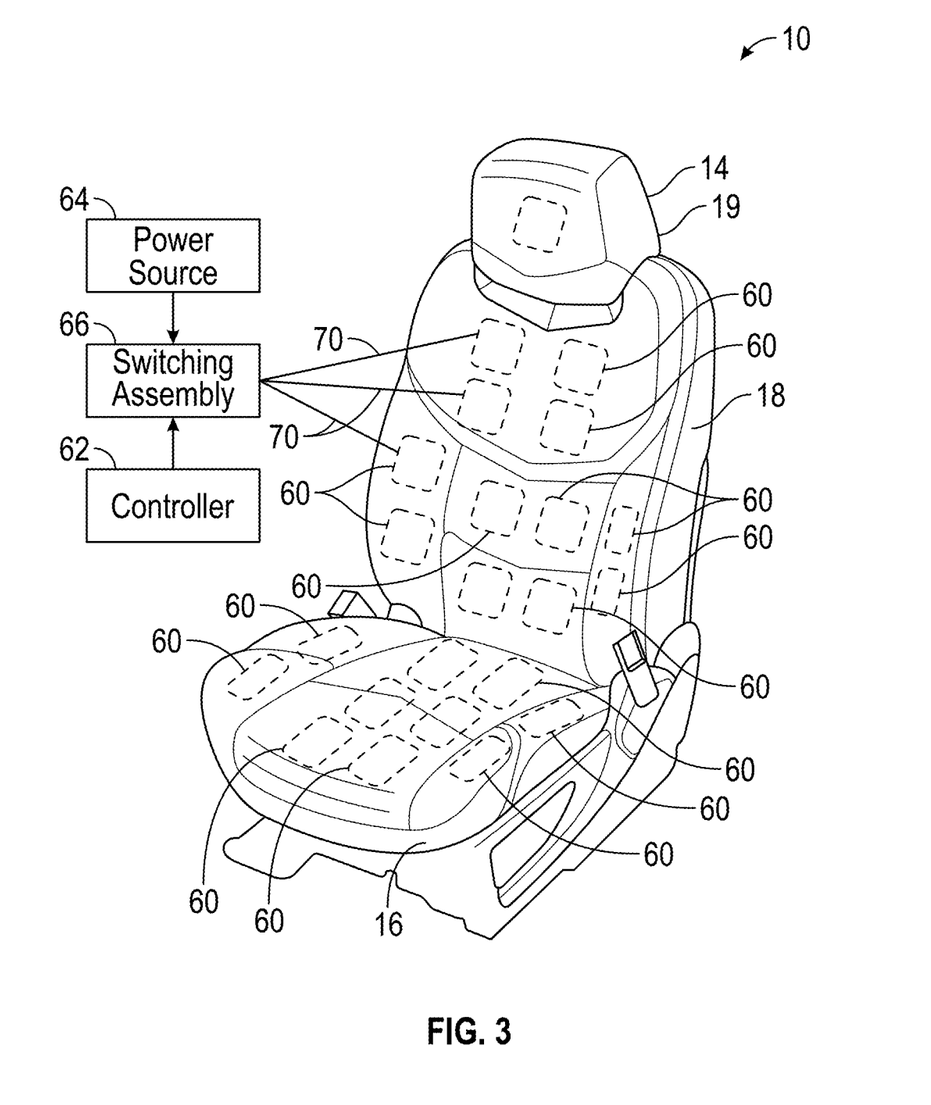
FIG. 3 is a perspective view of the seat assembly of FIG. 1 equipped with a localized heating or cooling therapy.

Referring now to FIG. 3 and as described above, the seat assembly 14 further includes localized heating and/or cooling therapy. The seating system 10 is designed to deliver localized heating and/or cooling from individually selectable areas of the seat assembly 14 to targeted anatomical areas of the person sitting in the seat assembly 14. One non-limiting intended use of the targeted heat and/or cooling is for the treatment of the person's pain resulting from musculoskeletal afflictions, soft tissue issues, internal organ afflictions, and the like. As an example, the heat and/or cooling delivered from seat assembly 14 to areas of the person in contact with the seat may have a temperature within a range of 10 to 45° C. at the occupant's skin level. However, it is contemplated that the seating system 10 may be configured to deliver heating and/or cooling for therapeutic benefits to a person sitting in the seat assembly 14 less than 10° C. or more than 45° C.

Referring again to FIG. 3, the seat assembly 14 includes a plurality of thermal units, thermal generation elements, and heating and/or cooling units, etc. (hereafter "thermal units") 60. The thermal units 60 are configured to generate heat and/or cooling. For instance, any of thermal units 60 may be embodied as classical resistive joule heating elements, Peltier resistive devices, direct infrared emission units, infrared generating fabrics, Peltier coolers, and the like. The thermal units 60 are distributed across seat bottom 14 and seat back 16. The seat bottom 14 and seat back 16 may be divided into any number of thermal units 60 based upon the seat design.

Referring again to FIG. 3, the thermal units 60 can be strategically arranged within seat assembly 14 to correspond with general anatomical locations of major muscle groups and/or organs of interest of a person sitting in the seat assembly 14. The thermal units 60 are configured to work independently of one another via a controller 62 such that they can function alone or in unison. It is also contemplated that in other embodiments, the thermal units 60 can be configured to work independently or in unison to sense localized pain and provide localized thermal tissue stimulation. In other embodiments, each of the thermal units 60 can be activated manually as needed by the seat assembly 14 occupant. Accordingly, the thermal units 60 are individually selectable and controllable to generate heat or cooling in response to pain and generate heat or cooling to affected anatomical areas of concern of an occupant of the seat assembly 14.

Referring again to FIG. 3, the seating system 10 further includes a power source 64 and a switching assembly 66. The power source 64 is configured to provide electrical power or energy for thermal units 60. The thermal units 60 convert energy supplied from power source 64 into heat and/or cooling. The switching assembly 66 is interposed between power source 64 and thermal units 60. For instance, as indicated in FIG. 3, the switching assembly 66 on the one hand is connected to the power source 64 and, on the other hand, is individually connected to the thermal units 60 via electrical conductors 70. As such, thermal units 60 are individually connected to receive power from power source 64 via switching assembly 66.

Referring again to FIG. 3, the controller 62 controls the switching assembly 66 to regulate power from power source 64 to thermal units 60. The controller 62 may also control the power source 64 to control the power (amplitude, frequency, etc.) supplied from the power source 64 to thermal units 60. In this way, the thermal units 60 are each adjustable and can be individually or collectively powered to generate heat or cooling.

Figure 4:
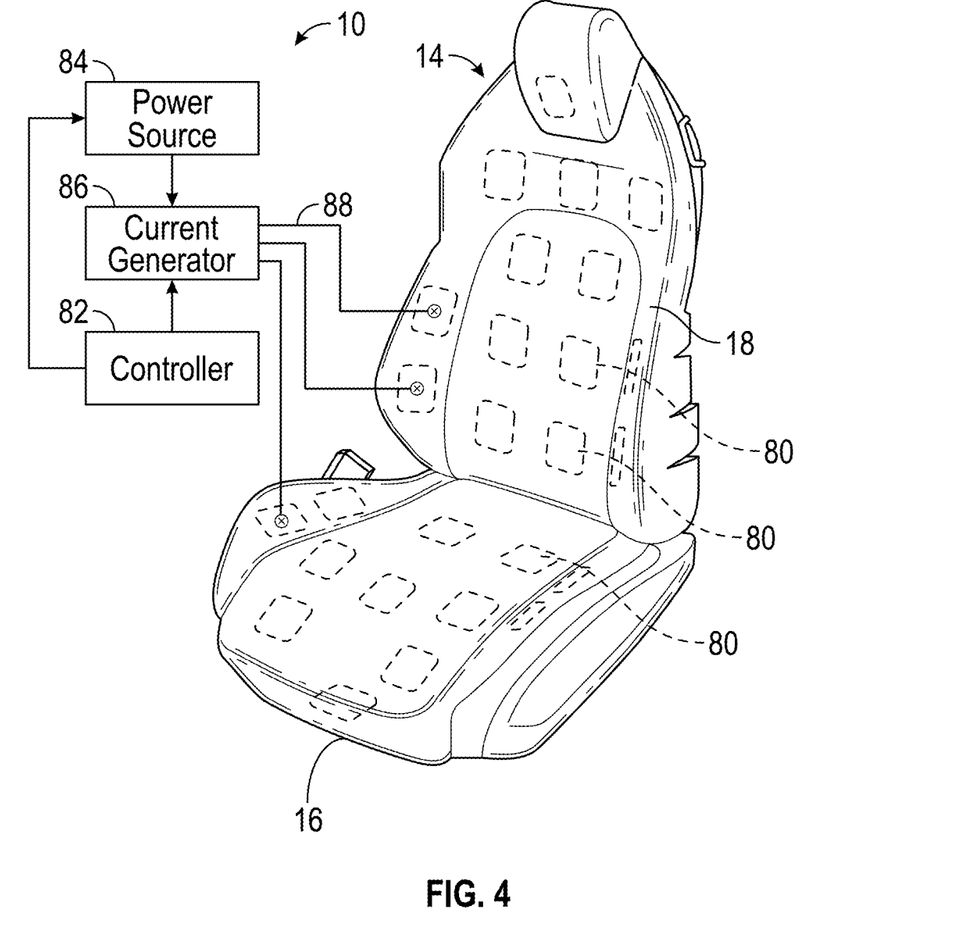
FIG. 4 is a perspective view of the seat assembly of FIG. 1 equipped with a pulsed electromagnetic field therapy system and a transcutaneous electrical nerve stimulation therapy system.

Referring now to FIG. 4 and as described above, the seat assembly 14 further includes a pulsed electromagnetic field therapy system (hereafter "pulsed therapy system") related to relieving inflammation and/or pain and stimulating tissue healing, and a transcutaneous electrical nerve stimulation therapy system (hereafter "nerve therapy system") further related to relieving inflammation and/or pain and stimulating tissue healing. One non-limiting example of a pulsed therapy system and a nerve therapy system is that described in U.S. Patent Application Publication No. 2018/0345833A1, which is incorporated in its entirety herein by reference and, for that reason, is only briefly described.

Referring again to FIG. 4, the seating system 10 is designed to deliver localized electromagnetic energy from individually selectable areas of seat assembly 14 to a person sitting in the seat assembly 14. In operation, the seating system 10 is configured to deliver electromagnetic energy targeted to affected anatomical areas of the person. An intended use of the targeted electromagnetic energy is for the treatment of the person's localized pain and discomfort resulting from musculoskeletal afflictions, soft tissue issues, and internal organ afflictions.

Referring again to FIG. 4, seat assembly 14 includes an array of electromagnetic coils 80. The electromagnetic coils 80 are configured to generate electromagnetic fields when activated. The electromagnetic coils 80 are distributed across the seat bottom 16 and the seat back 18. The seat bottom 16 and the seat back 18 are divided into any number of electromagnetic coils 80 based on the seat design.

Referring again to FIG. 4, the electromagnetic coils 80 can be strategically arranged within seat assembly 14 to correspond with general anatomical locations of major muscle groups of a person sitting in the seat assembly 14. The electromagnetic coils 80 are configured to work independently of one another via a controller 82 such that they can function alone or in unison to provide localized electromagnetic energy stimulation. As such, the electromagnetic coils 80 are individually selectable and controllable to generate electromagnetic fields. The electromagnetic coils 80 in different areas of seat assembly 14 can be selected individually or in any combination to deliver electromagnetic energy to affected anatomical areas of concern of an occupant of the seat assembly 14. In this way, each area of the seat assembly 14 can be selected individually or in any combination to match affected anatomical areas of concern of a person sitting in the seat.

Referring again to FIG. 4, the electromagnetic coils 80 can be made of various materials and shapes. The electromagnetic coils 80 can be constructed out of traditional wire with either a hollow or solid core. The electromagnetic coils 80 can be manufactured out of conductive fibers sewn or pressed into shape. The electromagnetic coils 80 can be integrated into the seat frame, seat cushion, seat back, seat side portions, seat foam, or into any portion of the seat trim, regardless of the form or nature of the seat trim. The electromagnetic coils 80 can exist separately between the foam and trim as stand-alone units. The geometry, placement, and materials of electromagnetic coils 80 depend upon intended use and location. The spatial density of the array of electromagnetic coils 80 can conform to seating design on a case-by-case basis.

Referring again to FIG. 4, the seating system 10 further includes a power source 84 and an electrical current generator 86. The current generator 86 is configured to generate alternating electrical currents (i.e., AC or time-varying electrical currents) and is further configured to use electrical power from the power source 84 to generate the currents. The current generator 86 is configured to provide the currents to electromagnetic coils 80. The electromagnetic coils 80 generate electromagnetic fields from being driven with the currents. Characteristics (e.g., intensity, frequency, etc.) of the electromagnetic fields generated by electromagnetic coils 80 correspond to characteristics (e.g., amplitude, frequency, etc.) of the currents supplied from current generator 86 to the electromagnetic coils.

Referring again to FIG. 4, the current generator 86 is individually connected to electromagnetic coils 80 via electrical conductors 88. In certain instances, the current generator 86 may have a plurality of output ports, which are respectively connected by electrical conductors 88 to respective electromagnetic coils 80. In these instances, the current generator 86 is individually connected to electromagnetic coils 80 to provide electrical currents to the electromagnetic coils 80.

Referring again to FIG. 4, the current generator 86 is configured to generate a plurality of unique electrical currents at any given time. The number of unique currents that current generator 86 can generate at any given time is at least the same number of output ports of the current generator 86. As such, current generator 86 is operable to provide unique currents respectively to electromagnetic coils 80 at any given time. Consequently, electromagnetic coils 80 generate unique electromagnetic fields in correspondence with the unique currents provided to the electromagnetic coils.

Referring again to FIG. 4, the electrical currents generated by the current generator 86 may have waveform or pulsed characteristics. In this way, the current generator 86 is a waveform or pulse generator. The uniqueness of a given current from other currents may be from unique waveform or pulsed characteristics of the given current.

Referring again to FIG. 4, the controller 82 is configured to control the current generator 86 in a manner such as to have the current generator 86 generate the electrical currents for electromagnetic coils 80. The controller 82 is configured to provide one or more control signals to current generator 86 for the current generator to generate one or more currents in correspondence with the one or more control signals. The control signals may include information that is indicative of characteristics (e.g., amplitude, frequency, intensity, strength, duration, continuous vs. pulse, shape (sinusoidal vs. triangle vs. square waveform), duration, repetition, etc.) that the currents are to have and information indicative of which electromagnetic coils 80 are to receive such currents. The currents may be unique from one another by having different characteristics. In other words, the characteristics of the currents may be different from one another whereby the currents are unique from one another. As one non-limiting example, the controller 82 provides to current generator 86 a control signal that includes information indicating that the current generator 86 is to generate an electrical current "A" for all of the electromagnetic coils 80. The current generator 86, in response to the control signal, generates and provides the current "A" to all of the electromagnetic coils 80. In turn, each electromagnetic coil 80 generates an electromagnetic field in correspondence with being driven by the current "A."

Referring again to FIG. 4, in another non-limiting example, the controller 82 provides the current generator 86 with a first control signal that includes information indicating that the current generator 86 is to generate an electrical current "A" for a first one of electromagnetic coils 80 and provides the current generator 86 with a second control signal which includes information indicating that the current generator 86 is to generate an electrical current "B" for a second one of electromagnetic coils 80. The current generator 86, in response to the first and second control signals, generates and provides the current "A" to the first one of electromagnetic coils 80 and generates and provides the current "B" to the second one of electromagnetic coils 80. In turn, the first one of electromagnetic coils 80 generates an electromagnetic field in correspondence with being driven by the current "A" and the second one of electromagnetic coils 80 generates an electromagnetic field in correspondence with being driven by the current "B."

Referring again to FIG. 4 in summary, the controller 82 is configured to provide unique control signals to current generator 86. The current generator 86 generates unique electrical currents in correspondence with the control signals and provides the currents to selected ones of electromagnetic coils 80. The selected ones of electromagnetic coils 80 generate electromagnetic fields in correspondence with the unique currents provided to the selected ones of the electromagnetic coils 80. In this way, electromagnetic coils 80 are each adjustable and can be individually or collectively powered to generate electromagnetic fields. The controller 82 may also control power source 84 to control the electrical power supplied from the power source to current generator 86.

As described, the seating system 10 provides a time-varying electromagnetic field stimulation system in vehicle seating designed to penetrate soft tissue, joints, and portions of internal organs of the person sitting in the seat assembly 14 to increase mobility and/or reduce pain and discomfort of the affected anatomical areas of the person. The seat bottom 16 and the seat back 18 are populated with electromagnetic coils 20. Electromagnetic coils 20, per the properties of electromagnetism, produce electromagnetic fields when alternating or time-varying electrical currents are applied to the electromagnetic coils. Rapidly changing electromagnetic field pulses induce a physiological response in the application area of the person sitting in the seat assembly 14. The current generator 86 and the controller 82, in cooperation, can control the electromagnetic coils 80 to vary the electromagnetic field pulsation frequency, duration, sequence, etc., to target specific types of stimulation and effects. The array of electromagnetic coils 80 can be strategically positioned within the seat assembly 14 and independently controlled to produce unique electromagnetic field shapes and strengths at the surface of the seat assembly 14.

Figure 5:
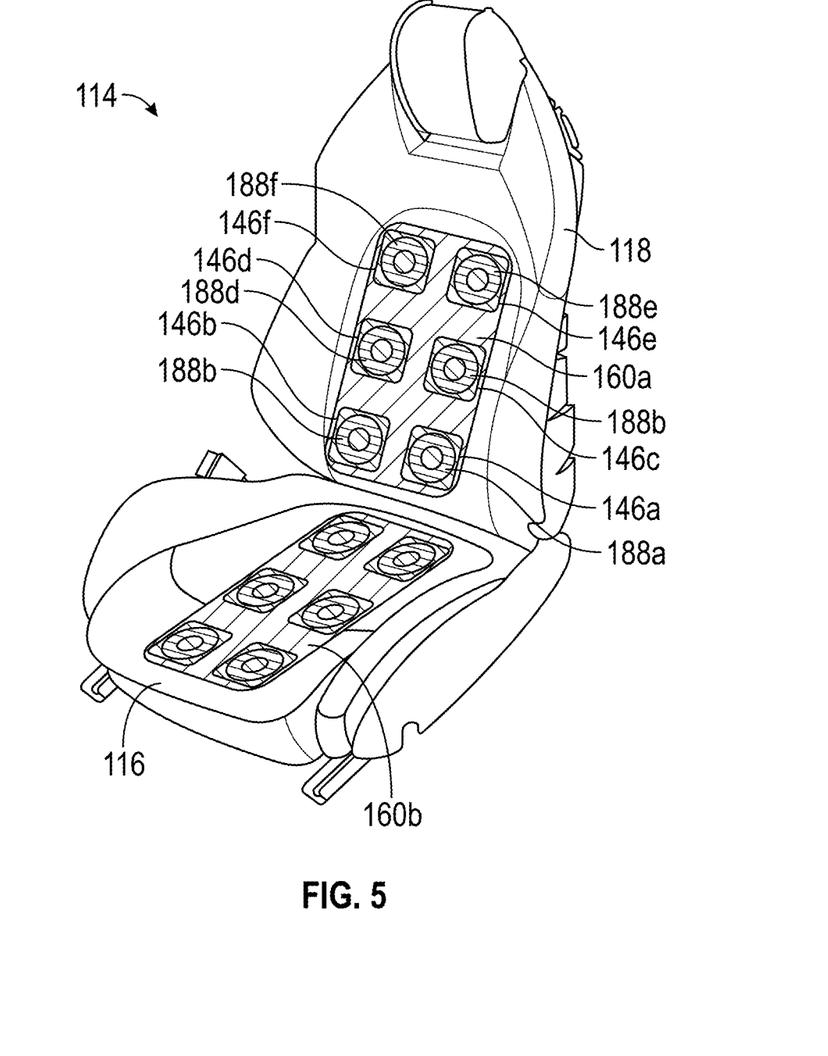
FIG. 5 is a perspective view of the seat assembly of FIG. 1 equipped with a combination of a massage therapy therapeutic technology, a localized heating or cooling therapy, a pulsed electromagnetic field therapy system, and a transcutaneous electrical nerve stimulation therapy system.

Referring now to FIG. 5, the various therapeutic technologies are combined into a seat assembly 114. The seat assembly 114 includes one or more thermal generation element assemblies 160a. The thermal generation element assemblies 160a are positioned in the seat back 118 and can be selected individually or in any combination and are configured to deliver heat or cooling to affected anatomical areas of concern of an occupant of the seat assembly 114. In the illustrated embodiment, the thermal generation element assemblies 160a are the same as, or similar to, the thermal generation elements 60 described above and illustrated in FIG. 3. In alternate embodiments, the thermal generation element assemblies 160a can be different from the thermal generation elements 60.

Referring again to FIG. 5, the seat assembly 114 further includes a plurality of air bladder assemblies 146a-146f. The air bladder assemblies 146a-146f are positioned in the seat back 118 and can be selected individually or in any combination to generate massage, repositioning, a side-to-side, and fore-aft shifting of the body weight to reduce pressure, pain, and discomfort generated by a stationary position and to mitigate pain-related syndromes or pain having other origins. In the illustrated embodiment, the air bladder assemblies 146a-146f are the same as, or similar to, the air bladder assemblies 46a-46d, 48a, and 48b described above and illustrated in FIG. 2. However, in alternate embodiments, the air bladder assemblies 146a-146f can be different from the air bladder assemblies 46a-46d, 48a, and 48b.

Referring again to FIG. 5, the seat assembly 114 further includes a plurality of electromagnetic coil assemblies 188a-188f. The electromagnetic coil assemblies 188a-188f are positioned in the seat back 118 and, once activated, can be selected individually or in any combination to penetrate soft tissue, joints, and portions of internal organs of the person sitting in the seat assembly 114, to increase mobility and/or reduce pain and discomfort of the affected anatomical areas of the person. In the illustrated embodiment, the electromagnetic coil assemblies 188a-188f are the same as, or similar to, the electromagnetic coils 80 described above and illustrated in FIG. 4. However, in alternate embodiments, the electromagnetic coil assemblies 188a-188f can be different from the electromagnetic coils 80.

Referring again to FIG. 5, in operation, combined countermeasures can be implemented in the event of localized muscle pain or other pain-related syndromes. The combined countermeasure can involve massage sequence provided by the plurality of air bladder assemblies 146a-146f, localized heating or cooling provided by the thermal generation element assemblies 160a, and electromagnetic stimulation therapy provided by the electromagnetic coil assemblies 188a-188f. The combined countermeasures can be deployed either continuously, non-continuously but synchronously between the various systems, continuously and asynchronously between the various systems, and/or both continuously and asynchronously between the various systems.

Referring again to FIG. 5, the one or more thermal generation element assemblies 160a, the plurality of air bladder assemblies 146a-146f, and the plurality of electromagnetic coil assemblies 188a-188f can be integrated into the seat frame, the seat cushion, the seat back, the seat side portions, the seat foam, or into any portion of the seat trim (regardless of the form or nature of the seat trim), the headrest, or a combination thereof. It is also contemplated that the one or more thermal generation element assemblies 160a, the plurality of air bladder assemblies 146a-146f, and the plurality of electromagnetic coil assemblies 188a-188f can be positioned in other vehicle locations, such as the non-limiting example of a steering wheel, and can be configured to operate on the driver's hands.

Referring again to FIG. 5, it should be appreciated that the one or more thermal generation element assemblies 160a, the plurality of air bladder assemblies 146a-146f, and the plurality of electromagnetic coil assemblies 188a-188f can be configured differently for the driver of the vehicle and the passengers, and further can be customized for different external and internal conditions.

Referring again to FIG. 5, the one or more thermal generation element assemblies 160a, the plurality of air bladder assemblies 146a-146f, and the plurality of electromagnetic coil assemblies 188a-188f can optionally be integrated into the seat bottom 116 in a manner similar to the seat back 118.

Referring again to FIG. 5, it is further contemplated that the seat assembly 114 can be used in an autonomous vehicle or a semi-autonomous vehicle.

The principle and mode of operation of the therapeutic technology fusion have been explained and illustrated in certain embodiments. However, it must be understood that the therapeutic technology fusion may be practiced otherwise than as specifically explained and illustrated without departing from its spirit or scope.

What is claimed is:

1. A system comprising:
   a controller; and
   one or more thermal generation element assemblies, or one or more air bladder assemblies, or one or more electromagnetic coil assemblies, or a combination thereof, that are configured for activation by the controller to provide an effect on an occupant of a vehicle, wherein either:
   (1) the one or more thermal generation element assemblies, or the one or more air bladder assemblies, or the one or more electromagnetic coil assemblies, or the combination thereof, are activated in response to fidgeting of the occupant; or
   (2) each of the one or more electromagnetic coil assemblies is configured to produce a pulsed electromagnetic field therapy on the occupant; or
   (3) each of the one or more electromagnetic coil assemblies is configured to produce a transcutaneous electrical nerve stimulation therapy on the occupant.

2. The system of claim 1, wherein the one or more thermal generation element assemblies, or the one or more air bladder assemblies, or the one or more electromagnetic coil assemblies, or the combination thereof, are activated in response to fidgeting of the occupant.

3. The system of claim 1, wherein the system is manually activated.

4. The system of claim 1, wherein each of the one or more thermal generation element assemblies is configured to provide heating or cooling.

5. The system of claim 1, wherein each of the one or more air bladder assemblies includes a plurality of lumbar air bladder assemblies, upper, mid, and lower thoracic air bladder assemblies, upper and lower left side bolster air bladder assemblies, upper and lower right side bolster air bladder assemblies, and bottom air bladder assemblies.

6. The system of claim 1, wherein each of the one or more the electromagnetic coil assemblies is configured to produce a pulsed electromagnetic field therapy on the occupant.

7. The system of claim 1, wherein each of the one or more the electromagnetic coil assemblies is configured to produce a transcutaneous electrical nerve stimulation therapy on the occupant.

8. A seat assembly comprising:
   a seat;
   a controller; and
   one or more thermal generation element assemblies, or one or more air bladder assemblies, or one or more electromagnetic coil assemblies, or a combination thereof, that are positioned in the seat and are configured for activation by the controller to provide an effect on an occupant of the seat, wherein either:
   (1) the one or more thermal generation element assemblies, or the one or more air bladder assemblies, or the one or more electromagnetic coil assemblies, or the combination thereof, are activated in response to fidgeting of the occupant; or
   (2) each of the one or more electromagnetic coil assemblies is configured to produce a pulsed electromagnetic field therapy on the occupant; or
   (3) each of the one or more electromagnetic coil assemblies is configured to produce a transcutaneous electrical nerve stimulation therapy on the occupant.

9. The seat assembly of claim 8, wherein the controller is configured to activate the one or more thermal generation element assemblies, or the one or more air bladder assemblies, or the one or more electromagnetic coil assemblies, or a combination thereof in response to fidgeting of the seat vehicle occupant.

10. The seat assembly of claim 8, wherein the controller is manually activated.

11. The seat assembly of claim 8, wherein each of the one or more thermal generation element assemblies is configured to provide heating or cooling.

12. The seat assembly of claim 8, wherein each of the one or more air bladder assemblies includes a plurality of lumbar air bladder assemblies, upper, mid, and lower thoracic air bladder assemblies, upper and lower left side bolster air bladder assemblies, upper and lower right side bolster air bladder assemblies, and bottom air bladder assemblies.

13. The seat assembly of claim 8, wherein each of the one or more electromagnetic coil assemblies is configured to produce a pulsed electromagnetic field therapy.

14. The seat assembly of claim 8, wherein each of the one or more electromagnetic coil assemblies is configured to produce a transcutaneous electrical nerve stimulation therapy.

15. A method comprising the steps of:
positioning one or more thermal generation element assemblies, or one or more air bladder assemblies, or one or more electromagnetic coil assemblies, or a combination thereof, within a seat assembly; and
activating the one or more of the thermal generation element assemblies, or the one or more of the air bladder assemblies, or the one or more of the electromagnetic coil assemblies to provide an effect on an occupant of the seat assembly, wherein either:
(1) the one or more thermal generation element assemblies, or the one or more air bladder assemblies, or the one or more electromagnetic coil assemblies, or the combination thereof, are activated in response to fidgeting of the occupant; or
(2) each of the one or more electromagnetic coil assemblies is configured to produce a pulsed electromagnetic field therapy on the occupant; or
(3) each of the one or more electromagnetic coil assemblies is configured to produce a transcutaneous electrical nerve stimulation therapy on the occupant.

16. The method of claim 15, including the step of providing heating or cooling with the one or more thermal generation element assemblies.

17. The method of claim 15, wherein each of the one or more air bladder assemblies includes a plurality of lumbar air bladder assemblies, upper, mid, and lower thoracic air bladder assemblies, upper and lower left side bolster air bladder assemblies, upper and lower right side bolster air bladder assemblies, and bottom air bladder assemblies.

18. The method of claim 15, including the step of activating the one or more thermal generation element assemblies, or the one or more air bladder assemblies, or the one or more electromagnetic coil assemblies, or the combination thereof are activated in response to fidgeting of the occupant.

19. The method of claim 15, including the step of producing a pulsed electromagnetic field therapy with the one or more electromagnetic coil assemblies.

20. The method of claim 15, including the step of producing a transcutaneous electrical nerve stimulation therapy with the one or more electromagnetic coil assemblies.

* * * * *